US012036729B2

(12) United States Patent
Cully et al.

(10) Patent No.: US 12,036,729 B2
(45) Date of Patent: Jul. 16, 2024

(54) PROCESS FOR FORMING POROUS THREE DIMENSIONAL EXPANDED POLYTETRAFLUOROETHYLENE ARTICLES

(71) Applicants: W. L. Gore & Associates, Inc., Newark, DE (US); W. L. Gore & Associates GmbH, Putzbrunn (DE)

(72) Inventors: Edward H. Cully, Newark, DE (US); Lawrence A. Ford, Munich (DE); Alexander Zaggl, Aying (DE)

(73) Assignees: W. L. Gore & Associates, Inc., Newark, DE (US); W. L. Gore & Associates GmbH, Putzbrunn (DE)

( * ) Notice: Subject to any disclaimer, the term of this patent is extended or adjusted under 35 U.S.C. 154(b) by 74 days.

(21) Appl. No.: 17/362,861

(22) Filed: Jun. 29, 2021

(65) Prior Publication Data
US 2022/0001602 A1    Jan. 6, 2022

Related U.S. Application Data

(60) Provisional application No. 63/046,840, filed on Jul. 1, 2020.

(51) Int. Cl.
*B29C 64/147*    (2017.01)
*A61F 2/30*    (2006.01)
(Continued)

(52) U.S. Cl.
CPC .......... *B29C 64/147* (2017.08); *A61F 2/3094* (2013.01); *B33Y 10/00* (2014.12);
(Continued)

(58) Field of Classification Search
CPC ......... B32B 37/00–30; B32B 2307/726–7265; B32B 2307/712; B29C 64/147; A61F 2002/30971; A61F 2002/30973
See application file for complete search history.

(56) References Cited

U.S. PATENT DOCUMENTS 3,953,566 A    4/1976    Gore
4,478,898 A    10/1984    Kato
(Continued)

FOREIGN PATENT DOCUMENTS

WO    1996040307 A1    12/1996

OTHER PUBLICATIONS

Au AK, Huynh W, Horowitz LF, Folch A. 3D-Printed Microfluidics. Angew Chem Int Ed Engl. Mar. 14, 2016;55(12):3862-81. doi: 10.1002/anie.201504382. Epub Feb. 8, 2016. PMID: 26854878; PMCID: PMC7679199, https://www.ncbi.nlm.nih.gov/pmc/articles/PMC7679199/ (accessed Nov. 19, 2022) (Year: 2016).*

(Continued)

*Primary Examiner* — Philip C Tucker
*Assistant Examiner* — Andrew L Swanson (57) ABSTRACT

An additive manufacturing process is provided to produce integral 3-dimensional (3D) articles by laminating together a plurality of expanded polytetrafluoroethylene (ePTFE) membranes. The process includes repetitive cycles of ePTFE membrane lamination paired with laser cutting/bonding to produce a desired geometry based on a pre-defined pattern. The process may be practiced manually or may be configured to work with commercially available LOM machines/systems developed for use with other roll-to-roll processible materials, such as paper.

11 Claims, 13 Drawing Sheets

(51) Int. Cl.
    *B33Y 10/00*    (2015.01)
    *B33Y 80/00*    (2015.01)
    *B29K 27/18*    (2006.01)
    *B29L 31/00*    (2006.01)

(52) U.S. Cl.
    CPC ..... *B33Y 80/00* (2014.12); *A61F 2002/30985* (2013.01); *B29K 2027/18* (2013.01); *B29L 2031/753* (2013.01)

(56) References Cited

U.S. PATENT DOCUMENTS

| | | | |
|---|---|---|---|
| 4,895,751 A | | 1/1990 | Kato et al. |
| 5,730,817 A * | | 3/1998 | Feygin .................. B29C 64/147 |
| | | | 156/359 |
| 5,997,681 A * | | 12/1999 | Kinzie .................... B29C 64/40 |
| | | | 156/263 |
| 6,075,180 A | | 6/2000 | Sharber et al. |
| 6,484,776 B1 * | | 11/2002 | Meilunas ................ B32B 37/00 |
| | | | 156/581 |
| 8,460,607 B2 | | 6/2013 | Yang |
| 8,784,983 B2 | | 7/2014 | Hisano et al. |
| 8,895,139 B2 | | 11/2014 | Roberts |
| 10,243,295 B2 | | 3/2019 | Matlack et al. |
| 10,919,217 B2 | | 2/2021 | Nauka et al. |
| 11,148,361 B2 | | 10/2021 | Jiang et al. |
| 11,179,886 B2 | | 11/2021 | Jiang et al. |
| 11,230,053 B2 | | 1/2022 | Bartow et al. |
| 2009/0101271 A1 | | 4/2009 | Ishida |
| 2012/0048800 A1 * | | 3/2012 | Farzana .................. B32B 37/02 |
| | | | 156/308.2 |
| 2015/0039097 A1 | | 2/2015 | Biris |
| 2015/0136318 A1 * | | 5/2015 | Tiefel .................... B29C 66/342 |
| | | | 156/272.8 |
| 2018/0131124 A1 * | | 5/2018 | Matlack ................ F04D 29/086 |

OTHER PUBLICATIONS

Hizawa T, Takano A, Parthiban P, Doyle PS, Iwase E, Hashimoto M. Rapid prototyping of fluoropolymer microchannels by xurography for improved solvent resistance. Biomicrofluidics. Dec. 14, 2018;12(6):064105. doi: 10.1063/1.5051666. PMID: 30867866; PMCID: PMC6404952. (Year: 2018).*

Mikos et al., Laminated Three-Dimensional Biodegradable Foams for Use in Tissue Engineering, Biomaterials 1993 vol. 15 No. 5 323-330.

* cited by examiner

Break away of support structure

Cross-section SEM view – ePTFE stays porous

Imbibed ePTFE-THV film laser cut on build platform

PROCESS FOR FORMING POROUS THREE DIMENSIONAL EXPANDED POLYTETRAFLUOROETHYLENE ARTICLES

FIELD

The present disclosure relates generally to three dimensional printing, and more specifically, to a method of printing a three dimensional article using expanded polytetrafluoroethylene.

BACKGROUND

Additive Layer Manufacturing (ALM) is a well-known process of joining layers of materials to build three-dimensional (3D) objects. In ALM 3D parts are built up with successive layers of material under computer control. One type of ALM is Laminated Object Manufacturing (LOM), a very fast and inexpensive way to 3D print objects. LOM forms a desired object by bonding together a plurality of substrate sheets cut in a target geometry according to a desired 3D model. However, many of the materials currently used for LOM do not possess properties required for certain applications such as strength, chemical inertness, porosity, and biocompatibility.

Polytetrafluoroethylene is a synthetic fluoropolymer having numerous applications due to its low surface energy, chemical inertness, low coefficient of friction, and biocompatibility. Crystalline PTFE can be expanded to form expanded polytetrafluoroethylene (ePTFE) and used to form mechanically strong, porous articles, such as tapes, tubes, fibers, and membranes as describes in U.S. Pat. No. 3,953,556 to Gore.

Recently, the 3M Company (Dyneon GmbH) introduced a stereolithographic process to three dimensionally print objects made from PTFE. However, the stereolithographic process does not produce objects having the mechanical strength provided by expanding PTFE (ePTFE). ePTFE also has various microstructure(s) required in many medical and life sciences applications. As such, there remains a need to provide a process to 3D print objects comprised of ePTFE.

SUMMARY

An additive manufacturing process is provided to produce integral 3-dimensional (3D) articles by laminating together a plurality of expanded polytetrafluoroethylene (ePTFE) sheets. The process includes repetitive cycles of ePTFE sheet lamination paired with laser cutting/bonding to produce a desired geometry based on a predefined pattern. The process may be practiced manually or may be configured to work with commercially available LOM machines/systems developed for use with other roll-to-roll processible materials, such as paper.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

As shown in FIG. 11C, a three-dimensional object in the shape of a human nose (1100) was created by using LOM with ePTFE in accordance with some embodiments;

DETAILED DESCRIPTION

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

As used herein, the phrase "at least one of A, B, and C" should be construed to mean a logical (A or B or C), using a non-exclusive logical OR. It should be understood that one or more steps within a method may be executed in different order (or concurrently) without altering the principles of the disclosure.

Terms such as "about," "approximately," "generally," "substantially," and the like, unless otherwise indicated, mean within plus/minus 10 percent of a given value or range. Numerical quantities given herein are approximate, meaning that the term "about," "approximately," "generally," or "substantially" can be inferred if not expressly stated.

It should be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

Further, relative terms, such as "lower" or "bottom" and "upper" or "top", may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

"Additive Layer Manufacturing (ALM)" or simply "additive manufacturing (AM)" are terms that encompass many others methods such as "3 dimensional (3D) printing", "3D printing", "rapid prototyping", "rapid manufacturing", "direct digital manufacturing", "laminated object manufacturing" (LOM) or "layered manufacturing" (LM). More generally, ALM qualifies any process that does not operate by subtractive manufacturing (e.g., where the material is removed to attain the desired shape). Instead, additive manufacturing is the process of joining materials to build objects from 3D model data, usually layer upon layer. While it is commonly referred to as "3D-printing", "additive manufacturing", "laminated object manufacturing" or "additive layer manufacturing" are the proper terms to use within the industrial scope.

As the term "elastomer" is used herein it defines a polymer that has the ability to be stretched to at least twice its original length and to retract rapidly to approximately its original length when released. The term "elastomeric" is intended to describe a condition whereby a polymer displays stretch and recovery properties similar to an elastomer, although not necessarily to the same degree of stretch and/or recovery.

As used herein, the term "thermoplastic" is used herein it is meant to define a polymer that softens when exposed to heat and returns to its original condition when cooled to room temperature. Such a polymer can be made to soften, flow, or take on new shapes without significant degradation or alteration of the polymer's original condition by the application of heat or heat and pressure.

In contrast to a thermoplastic polymer, a "thermoset" polymer as used herein is meant to describe a polymer that solidifies or "sets" irreversibly when cured. A determination of whether a polymer is a "thermoplastic" polymer within the meaning of the present invention can be made by slowly elevating the temperature of a stressed specimen and watching for deformation.

It is to be appreciated that expanded polytetrafluoroethylene is used herein for convenience, but expanded polyethylene may be equally utilized, and may be used interchangeable herein.

Expanded PTFE

The polymer forming the porous expanded membrane utilized to form the three dimensional (3D) articles described herein is inert and resistant to degradation within the environment of the target application. It is to be appreciated that the term "membrane" is used herein for convenience only. Tapes and/or films may also or alternatively be equally used herein. The polymer may be suitable for use in both in vivo or ex vivo use. In some embodiments, porous expanded polytetrafluoroethylene (ePTFE) membranes are used to form the 3D articles. It is to be understood that throughout this disclosure, the term polytetrafluoroethylene ("PTFE) is used for convenience, and is meant to include not only polytetrafluoroethylene but also expanded PTFE, modified PTFE, expanded modified PTFE, and expanded copolymers of PTFE, such as, for example, those described in U.S. Pat. No. 5,708,044 to Branca, U.S. Pat. No. 6,541,589 to Baillie, U.S. Pat. No. 7,531,611 to Sabol et al., U.S. Pat. No. 8,637,144 to Ford, and U.S. Pat. No. 9,139,669 to Xu et al.

In at least one embodiment, the materials used to form the PTFE may be a PTFE homopolymer or a blend of PTFE homopolymers. In another embodiment, the PTFE starting materials may be a blend of a PTFE homopolymer and a PTFE copolymer in which the comonomer units are not present in amounts that cause the copolymer to lose the inert characteristics of a pure homopolymer PTFE. Examples of suitable comonomers in the PTFE copolymer include, but are not limited to, olefins such as, but not limited to, ethylene and propylene; halogenated olefins such as hexafluoropropylene (HFP), vinylidene fluoride (VDF), and chlorofluoroethylene (CFE); perfluoroalkyl vinyl ether (PPVE), and perfluoro sulfonyl vinyl ether (PSVE).

In another embodiment, the PTFE precursor membrane may be formed by blending fibrillating PTFE polymer particles in a manner such as is generally taught in United States Publication No. 2005/0057888 to Mitchell, et al., United States Publication No. 2010/0119699 to Zhong, et al., U.S. Pat. No. 5,849,235 to Sassa, et al., U.S. Pat. No. 6,218,000 to Rudolf, et al., or U.S. Pat. No. 4,985,296 to Mortimer. Uniaxial, biaxial, and radial expansion are generally described in U.S. Pat. No. 3,953,566 to Gore and U.S. Pat. No. 4,478,665 to Hubis.

As used herein, the terms "PTFE membrane" and "ePTFE membrane" may be used interchangeably and refers to expanded porous polytetrafluoroethylene membranes that have a node and fibril microstructure. Fibril diameters may range from 2 µm to 100 µm, from 5 µm to 50 µm, or from 10 µm to 30 µm. Individual layers of the ePTFE membranes used in the 3D forming process may independently be uniaxially, biaxially, or radially oriented PTFE membranes. In one embodiment, the ePTFE membrane is uniaxially oriented. In another embodiment, the ePTFE membrane is biaxially oriented. The individual ePTFE membrane layers may independently have a thickness ranging from 2 µm to 500 µm, from 2 µm to 100 µm, or from 2 µm to 50 µm. It is to be appreciated that the use of thinner ePTFE membranes typically results in 3D articles with finer overall features. This is commonly referred to as the "resolution" of the process.

In some embodiments, the ePTFE membrane may further include one or more additional materials selected from thermoplastic polymers, elastomers, thermoset polymers, particulate fillers (e.g., pigments, metals, metal oxides, etc.), and any combination thereof. Examples of such polymers include, but are not limited to, polyamides (e.g., nylons), copolymers of polyamides (e.g., nylon-polyether copolymers), polyesters (e.g., polyethylene terephthalate (PET) polymers, polybutylene terephthalate (PBT) polymers), copolymers of polyesters, polyetheretherketones (PEEKs), polyurethanes, polyethylenes, polypropylenes, copolymers and ionomers of ethylene, copolymers and ionomers of polypropylene, polystyrenes and copolymers of polystyrenes. Non-limiting examples of commercially available polyesters include the Selar PT family of polymers (e.g., Selar PT 8307, Selar PT4274, Selar PTX280), which are commercially available from E. I. DuPont de Nemours (Wilmington, Del.), the Cleartuf family of polymers (e.g., Cleartuf 8006), which are commercially available from M and G Polymers (Apple Grove, W.V.), the Traytuf family of polymers (e.g., Traytuf 1006), which are commercially available from the Shell Chemical (Houston, Tex.), the Melinar family of polymers, commercially available from E. I. DuPont de Nemours (Wilmington, Del.), the Celanex family of polymers, commercially available from Ticona (Summit, N.J.), the Riteflex family of polymers, commercially available from Ticona (Summit, N.J.), the Hytrel family of polymers (e.g., Hytrel 5556, Hytrel 7246, Hytrel 4056), commercially available from E. I. DuPont de Nemours (Wilmington, Del.), the Arnitel family of polymers (e.g., Arnitel EM630), commercially available from DSM (Erionspilla, Ind.). Examples of commercially available polyamides include Nylon 12, commercially available from Atofina (Philadelphia, Pa.), Nylon 6, commercially available from Honeywell (Morristown, N.J.), Nylon 6/10, commercially available from BASF (Mount Olive, N.J.), Nylon 6/12, commercially available from Ashley Polymers (Cranford, N.J.), Nylon 11, Nylon MXD-6, and the Grivory family of polymers, commercially available from EMS (Sumter, S.C.), the Grilamid(R) family of polymers (e.g., Grilamid L25, Grilamid L20), commercially available from EMS (Sumter, S.C.), the Vestamid family of polymers (e.g., Vestamid L2101F), commercially available from Daicel-Degussa Ltd., and the PEBAX(R) family of polymers (e.g., PEBAX 5533, PEBAX 2533, PEBAX 7033), commercially available from Atofina (Philadelphia, Pa.), the Trogamid family of polyamides from Daicel-Degussa, Cristamid MS1100 from Atofina (Philadelphia, Pa.), and Vestamid L2101F nylon 12 from Degussa AG. An example of a commercially available polyethylene is Marlex 4903 high density polyethylene from Phillips 66 (Bartlesville, Okla.).

The individual ePTFE membranes within the 3D article may vary in porosity from layer to layer. The porosity of the individual layers may range from about 1%, about 25%, from about 1% to about 50%, from about 1% to about 75%, from about 1% to about 90%, or from 1% to about 95%, or from about 1% to about 99%, from about 25% to about 99%, from about 25% to about 90%, from about 50% to about 99%, from about 50% to about 90%, or from about 75% to about 90%. In some embodiments, the porosity of the individual layers may be greater than about 50%, greater than about 75%, or greater than about 90%.

In addition, the individual ePTFE membranes used in forming 3D objects may be independently symmetrical or asymmetrical depending upon the desired application. Asymmetric, as used herein, may include an asymmetry in pore size from one side of the ePTFE membrane to the opposing side of the ePTFE membrane. Symmetry as used herein is meant to define an ePTFE membrane that has the same pore size throughout the membrane.

In some embodiments, ePTFE composite membranes may be used. The ePTFE composite membranes may be used alone or in combination with the ePTFE membranes described herein. The ePTFE composite membranes may be include two or more layers of the polymers or PTFE membranes described above, such as in a stacked or layered configuration. In another embodiment, the ePTFE composite membrane may include one or more polymers at least partially imbibed within the pores of the porous ePTFE membrane. In a further embodiment, the ePTFE composite may be fully imbibed with one or more of the polymers described above.

In some instances, an ePTFE membrane with minimal porosity may be used to purposely segregate certain areas of the construct. As well, a fully dense expanded PTFE membrane may be achieved with pressure and heat. Such a densified membrane may be useful in the creation of internal microfluidic channels and hinges within the 3D construct. In some embodiments, the densified ePTFE membrane may be used as a barrier layer(s) within the 3D object.

Suitable Adhesives

The choice of suitable adhesives used in the present process may vary according to the target application. Suitable adhesives for use herein include thermoplastics, thermoplastic fluoropolymers (such as fluorinated ethylene propylene (FEP) and perfluoroalkoxy (PFA)), thermosets, polyurethane resins, polyimide resins, epoxy resins, polybutadiene resins, polyester resins, triazine resins, bis-maleimidotriazine resins, and mixtures of two or more such resins. The adhesive(s) may be cured or set by conventional methods including room temperature vulcanizine (RTV), ultraviolet, chemical, heat, pressure activation, or heat and pressure. For applications where the 3D article (e.g., 3D printed object) is as an implantable device, a regulatory approved and/or biologically acceptable adhesive is used. In some instances, the sintering of the substrate layers may provide enough structural strength to obviate the need of adhesives. In addition, the adhesives provided between individual layers of ePTFE may be the same or different, and they may have the same or different properties (e.g. hard or soft) depending on the desired application. In some embodiments, the adhesives provided between the ePTFE layers are alternate adhesives with different properties.

Laminated Object Manufacturing (LOM)

The 3D article may be formed manually (i.e., layers applied and bonded by hand) or it may be adapted to function with automated manufacturing systems using robotics and/or computer assisted design (CAD). In some embodiments, the process of forming the 3D article may include creating a 3D pattern based on a custom profile/measurement (e.g., creating a pattern based a patient's or person's specific need) and then fabricating the desired object using the process described herein. The 3D pattern may be created at a remote location (e.g., a hospital) and then transmitted (electronically or by non-electronic methods) to the manufacturing facility where the custom object will be fabricated. If needed, the fabricated 3D article may be shipped directly to the medical facility, treating physician, or patient.

Laser

Laminated Object Manufacturing (LOM) manufacturing may include the use of a laser to cut and/or shape the laminated object and/or the individual ePTFE membrane layers as they are applied. The laser is used to cut or bond layers of individual ePTFE membranes together by adjusting the relative power used. One or more lasers may be used to form the 3D article. In one embodiment, a single laser is used where the energy output is adjusted to achieve the desired effect (i.e., cutting vs. bonding). The laser beam may be focused so as to cut only one ePTFE membrane layer per pass. This allows the creation of numerous surface angles, contours, and steps to be conducted without damaging the ePTFE membrane layers below. When using the laser to bond ePTFE membranes, the laser power may be reduced or the laser beam may be de-focused (e.g., for a wider, lower power pass). Applied pressure on the ePTFE layered 3D article may be required during bonding. If so, vacuum may be applied at the base, such as through the use of a vacuum table. Since the ePTFE membrane layers are porous, a plate is typically used above the ePTFE membrane layers to apply pressure. A preferred material for this plate is Zinc Selenide glass, which will allow a $CO_2$ laser beam to pass through without distortion or damage. Although a $CO_2$ laser has demonstrated usefulness in this process, it is envisioned that other types of lasers and wavelengths may be equally useful. The use of a laser to cut and/or bond the various ePTFE membrane layers is particularly attractive as the edges of the ePTFE membrane remain porous. Porosity may be used in medical implants such as, but not limited to, subcutaneous augmentation materials (SAM).

End Use Articles Made from Current Process

Any number of 3D articles may be fabricated using the compositions and methods described herein. The present process is particularly attractive for rapid fabrication of custom fit medical implants or devices. The implants may be suitable for use in humans or non-humans (e.g., veterinary applications).

In some embodiments, the 3D article is a prosthetic medical implant or medical device. The prosthetic implant may be used to supplement, replace or repair soft and/or hard tissues including, but not limited to, bone, muscle, organs, cartilage, and tissues of the integumentary system or cardiovascular system. As well, some implants may be required to span across or through multiple anatomic structures. For example, an implant may need sections or layers that replicate bone, then cartilage, then muscle, then adipose tissue. The ALM process of the present disclosure will allow for the layering of sheets of material or membranes with various stiffness, hardness, porosity, strength, etc. This freedom of design allows for almost unlimited design variation during the engineering of the implant.

In another embodiment, LOM is used to fabricate custom prosthetic medical implants based on a pattern developed for a patient's specific need (such as prosthetic implants to correct birth defects, injuries and/or desired cosmetic alterations). These patterns may include spaces for specific structures, microstructures, or nanostructures to provide additional functionality, such as, but not limited to, attachment points/anchoring, regions to promote or restrict vascularization/tissue ingrowth, fluidic channels, and/or storage compartments for the delivery of beneficial agents.

In some embodiments, the 3D article may be a biological fluid sampling device. In a further embodiment, the biological fluid sampling device includes one more microfluid channels.

Very intricate and varied constructs may be produced by 1) controlling the characteristics of the individual ePTFE layers (e.g., strength, thickness, porosity, resin type, etc.), 2) controlling the direction or angle of lay-up, 3) controlling the areas of adhesion and/or ablation, and 4) controlling (and cutting) the outer periphery. In some embodiments, an initial step of forming a 3D pattern that is used to determine the desired pattern for each laser cut ePTFE membrane layer in the multilayered structure is performed.

In the case of producing mammalian implants (and depending upon the anatomical deficit being repaired), the implant may require many forms of porous material(s). Base layers (i.e., initial layers) may need to have very little porosity to prevent ingrowth and adhesion. Other layers may need fluidic channels. Layers nearer to the dermis may have the need for compressibility. The entire 3D article may need to conform in all directions, or to bend in one or more directions.

EXAMPLES

Example 1

A uniaxially expanded PTFE (ePTFE) membrane was made generally by the process disclosed in U.S. Pat. No. 3,953,566 to Gore. The formed porous, ePTFE membrane had a thickness of approximately 100 µm. The ePTFE membrane was coated with a coating polymer with a dot pattern using a continuous coating line with a gravure printing module. The coating polymer was a thermoplastic polyolefin hot melt adhesive JOWAT-TOPTHERM® PO, supplied by Jowat SE (Ernst-Hilker-Straße 10-14, D-32758 Detmold, Germany).

A 100 mm×100 mm aluminum platform (i.e., build plate) and a 2-sided high strength acrylic pressure sensitive adhesive tape (3M™ 950 Adhesive Transfer Tape, 3M Deutschland GmbH, Carl-Schurz-Str. 1, 41453 Neuss, Germany) were obtained. The two-sided pressure sensitive adhesive tape was utilized to increase base layer adhesion while still allowing for later removal of the individual ePTFE membrane layers.

Figure 1:
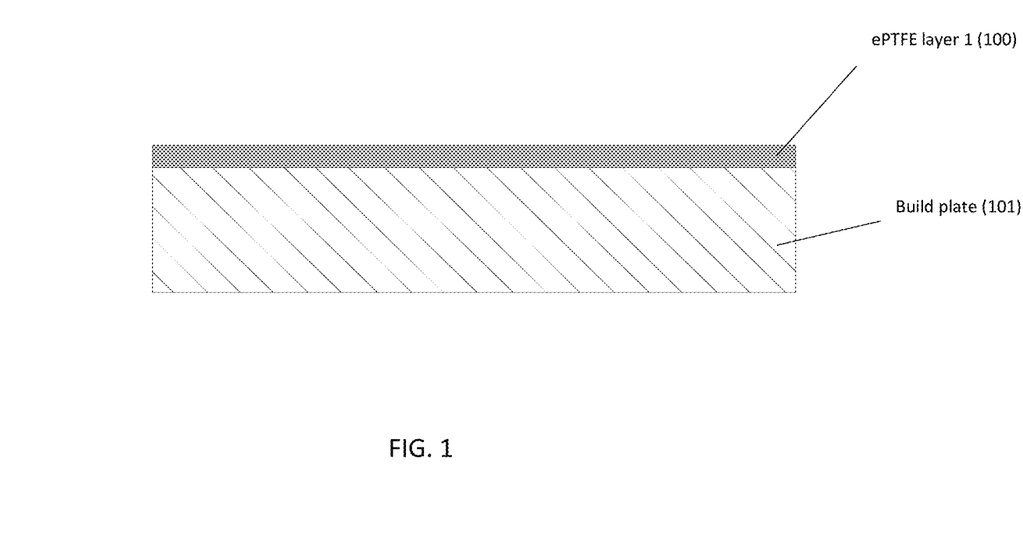
FIG. 1 shows a first ePTFE layer (100) adhered to a build plate (101) in accordance with some embodiments.

The dot printed ePTFE membrane was applied on the pressure sensitive adhesive using a hand roller (not illustrated) so as to apply the first ePTFE membrane layer 100 onto the build plate 101 (See, FIG. 1). The build plate 101 was then inserted into the edge of a laser cutter platform, model TROTEC® Speedy, supplied by TROTEC® Laser GmbH (Freilinger str. 99, 4614 Marchtrenk, Österreich, Germany).

A set of three-dimensional (3D) solid part models were then created in a CAD (computer assisted design) program and sliced to obtain 89 individual layers. The data for the individual layers was transferred to the laser cutter software.

Figure 7:
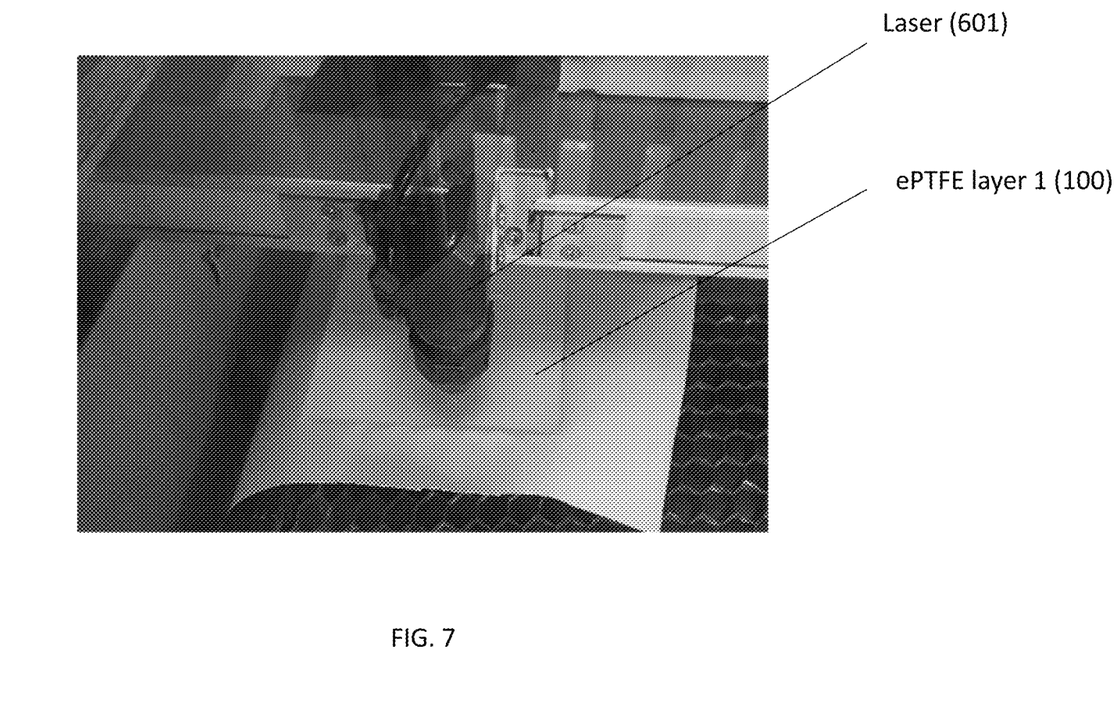
FIG. 7 is an image showing a laser cutter cutting a top layer of a first ePTFE layer in accordance with some embodiments.

Pre-trials were conducted by adjusting different settings of the laser cutter so as to be able to cut only 1 layer of the ePTFE membrane (e.g., not 2 ePTFE membranes). FIG. 7 is an image depicting a laser cutter cutting the top ePTFE layer, but not the underlying ePTFE membrane. These settings were used to cut the 89 layers. The laser was zeroed to the build plate. This was repeated for each ePTFE layer to assure that the laser was not out-of-focus. The first ePTFE membrane layer 100 was cut by the laser to form a laser cut 200 in the first ePTFE membrane layer 100 (FIG. 2).

Figure 3:
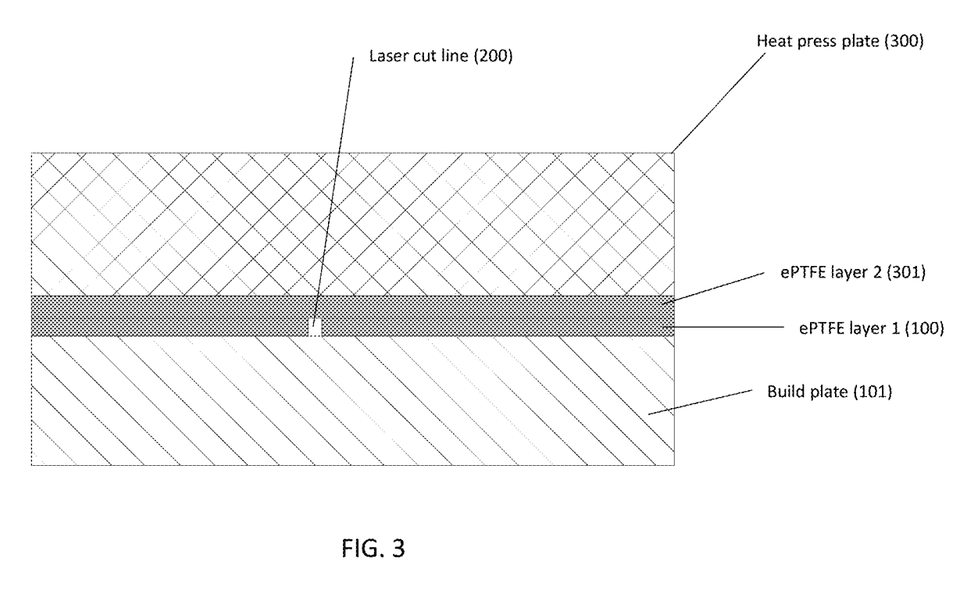
FIG. 3 shows multiple ePTFE layers including the first ePTFE (100) having a laser cut line (200) and a second ePTFE (300) sandwiched between the build plate (101) and the heat press (301) in accordance with some embodiments.

A second layer of ePTFE membrane 301 was then supplied and rolled onto the cut first ePTFE membrane layer 100 positioned on the build plate 101. The build plate 101 with the two ePTFE membrane layers (100, 301) were taken out of the laser cutter and inserted in a semi-automatic heat press 300 (Sefa Model MP 160, Sefa, BP44, Zi de Pastabrac, 11260 Esperaza, France) The heat press 300 settings were: 150° C., 2 Bar, and 10 seconds.

Figure 2:
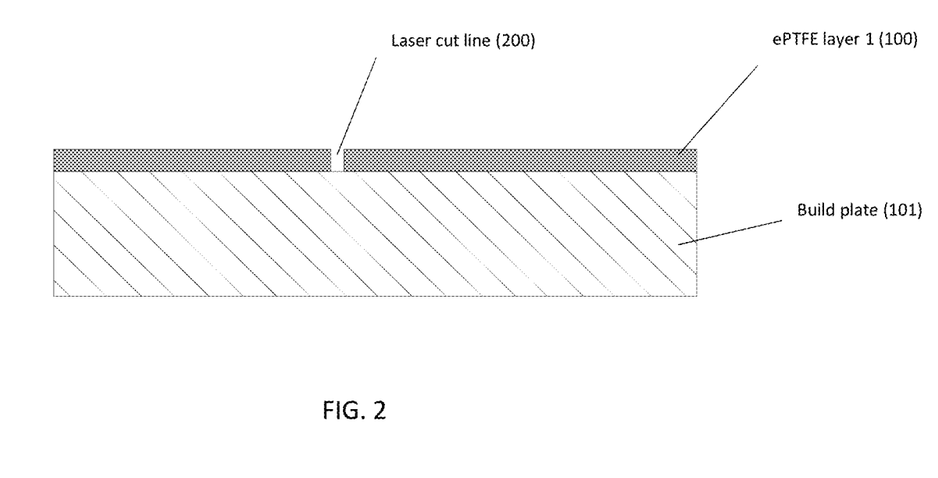
FIG. 2 shows a first ePTFE layer (100) with a laser cut line (200) and the build plate (101) in accordance with some embodiments.
Figure 4:
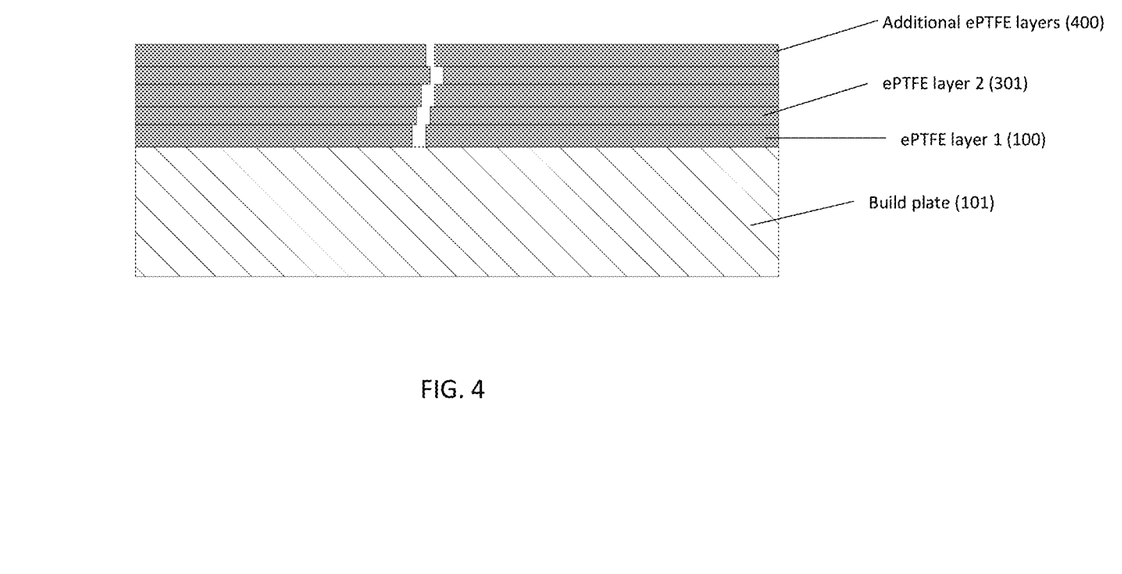
FIG. 4 shows additional ePTFE layers (400) that have been layered on top of the first ePTFE layer (100) and the second ePTFE layer 300 that are stacked on a build plate (101) in accordance with some embodiments.
Figure 8:
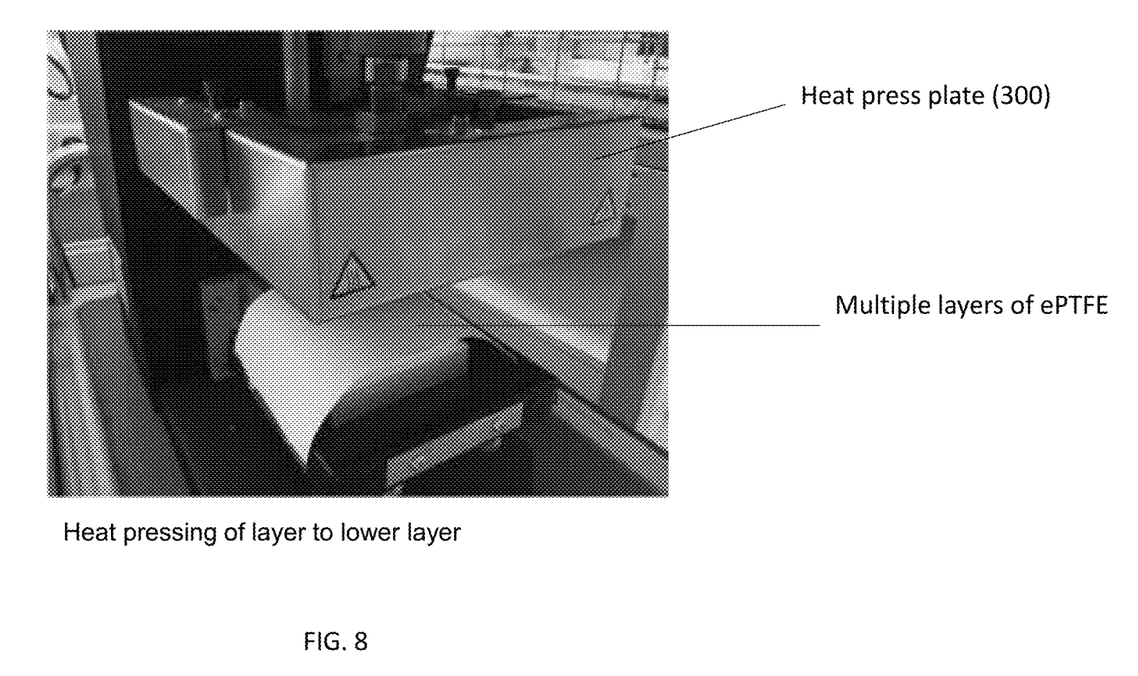
FIG. 8 is an image showing an exemplary heat press (300) used to press together multiple layers of ePTFE in accordance with some embodiments.
Figure 9:
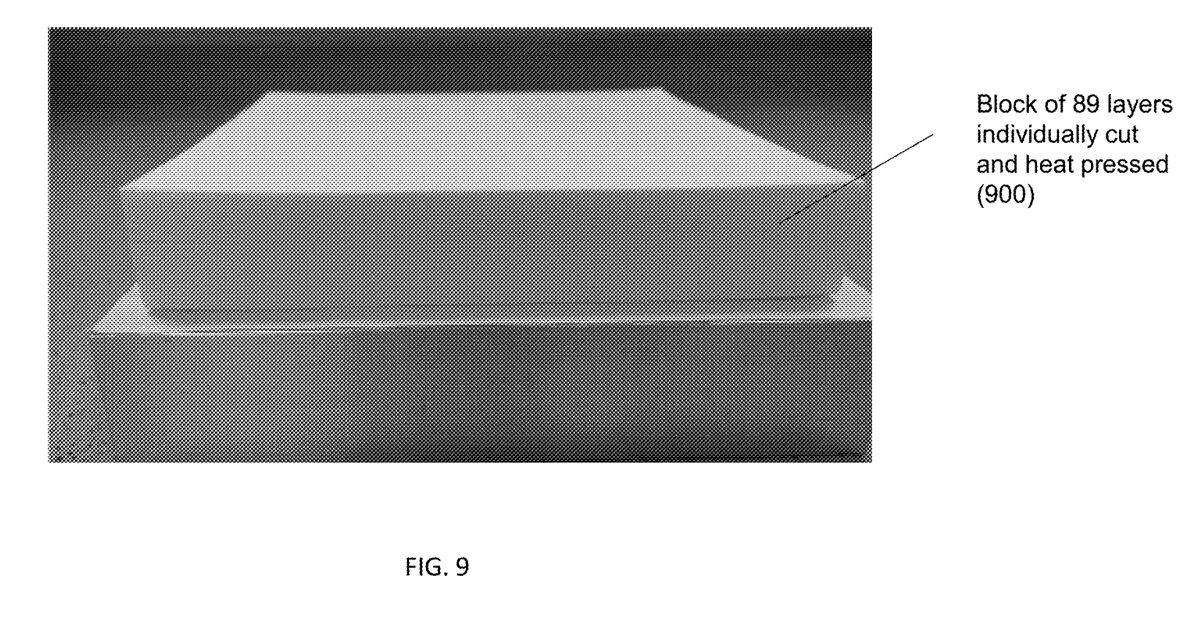
FIG. 9 is an image showing a block comprised of 89 individually cut and pressed together layers (900) of ePTFE membranes in accordance with some embodiments.
Figure 10:
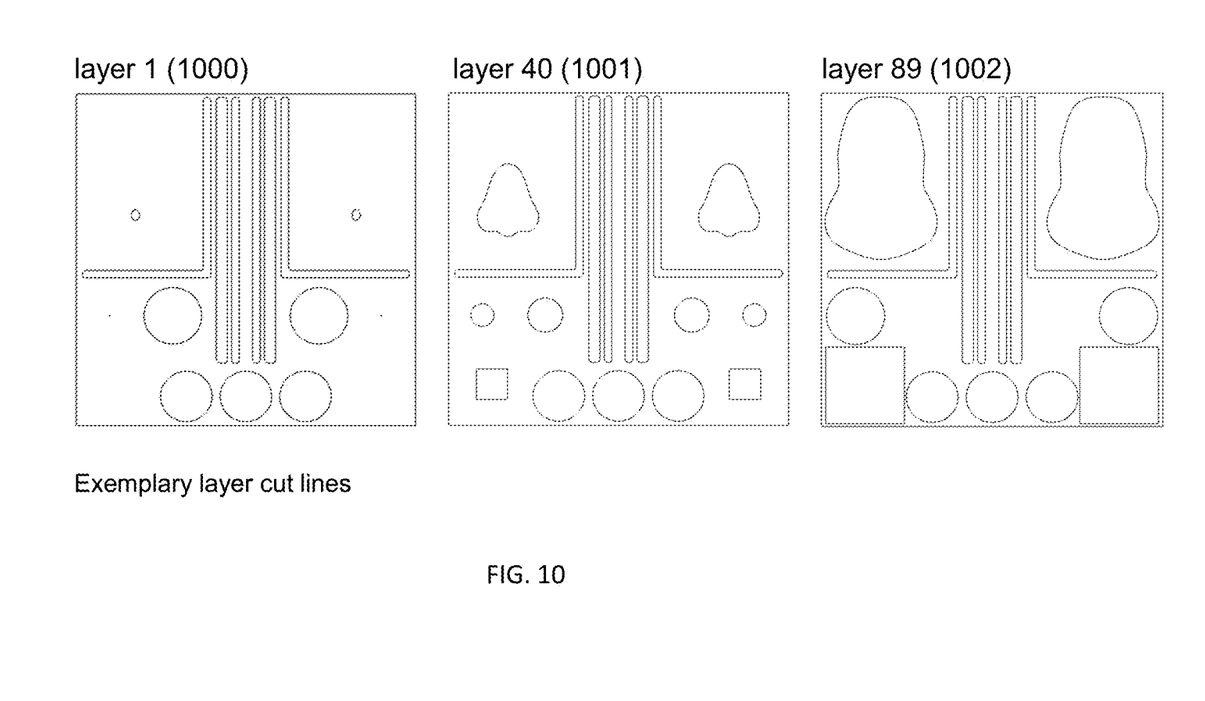
FIG. 10 shows examples of layer cut line/patterns within individual sheet layers when constructing a larger three-dimensional object in accordance with some embodiments.
Figure 11A:
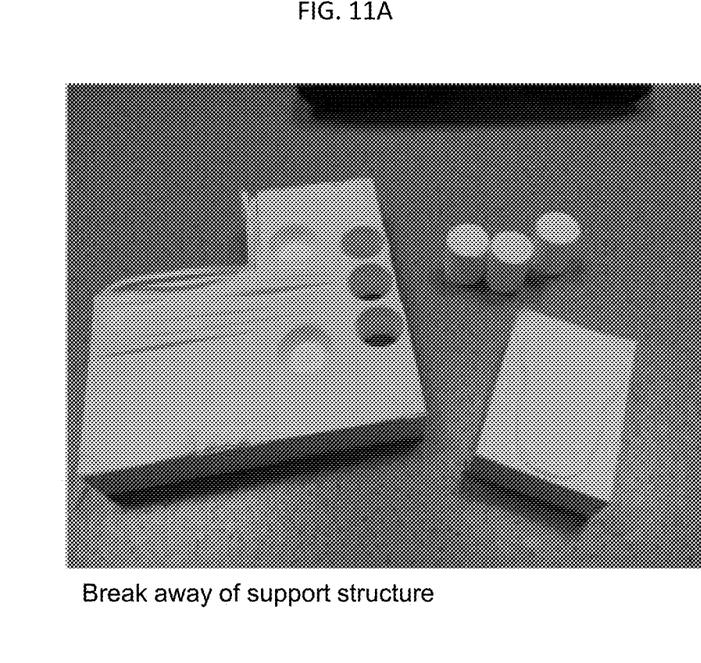
FIGS. 11A-11C are images showing the removal of support structures to obtain the desired three-dimensional object.
Figure 11B:
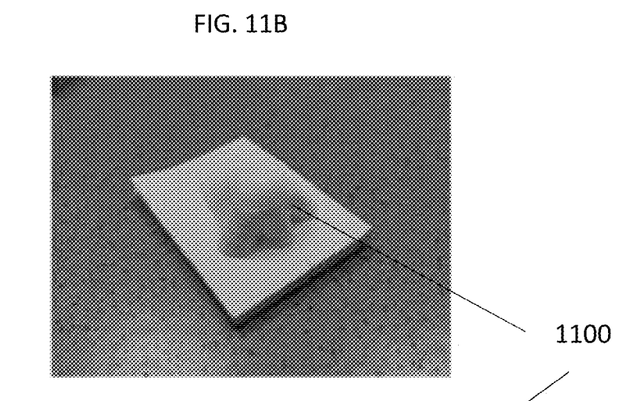
Figure 11C:
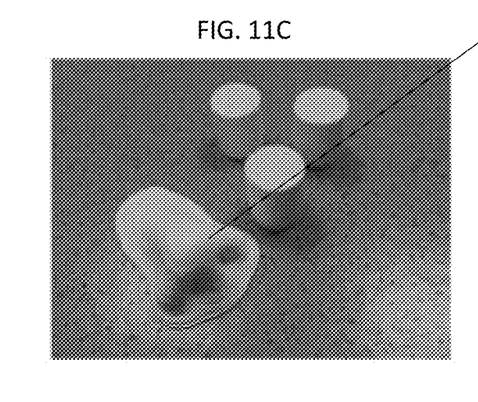

The process shown in FIGS. 1-3 was repeated (as described herein) for each of the remaining ePTFE membrane layers 400 (FIG. 4). FIG. 8 is an image showing a heat press 300 used to press together the multiple layers of ePTFE membrane. FIG. 9 is an image depicting a block of 89 individually cut and pressed together layers (900) of ePTFE membranes. FIG. 10 shows layer cut line/patterns within the individual sheet layers when constructing a three-dimensional object. Exemplified are layers 1 (1000), 40 (1001), and 89 (1002). The 3D articles were removed by cutting and breaking away the waste sections of the material. FIGS. 11A-11C are images showing the removal of the waste sections, or unwanted portions of the base material. As shown in FIG. 11C, a 3D article in the shape of a human nose (1100) was created by using LOM with ePTFE membranes.

Figure 12A:
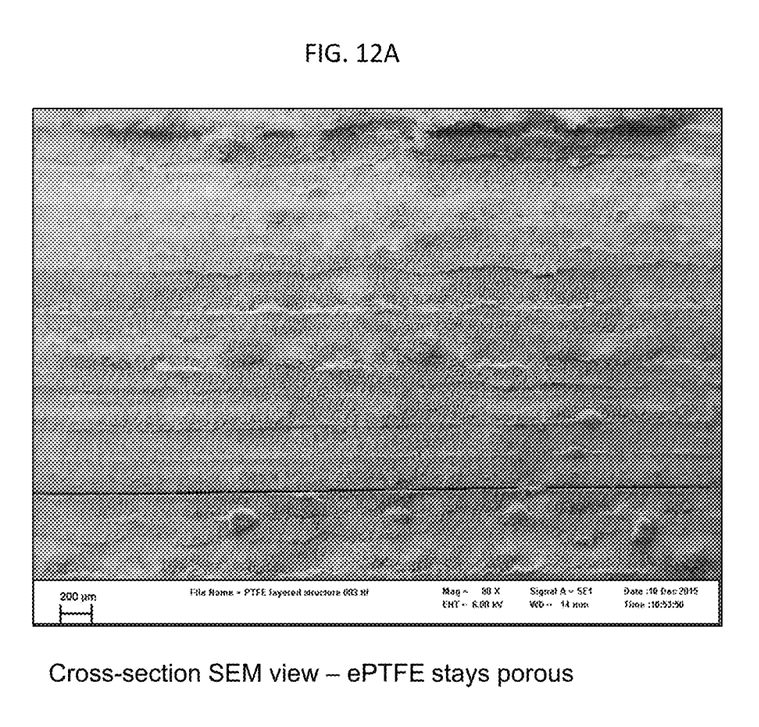
FIGS. 12A and 12B are side views SEMs showing that the laser cut ePTFE remains porous when creating three-dimensional objections by LOM in accordance with some embodiments.
Figure 12B:
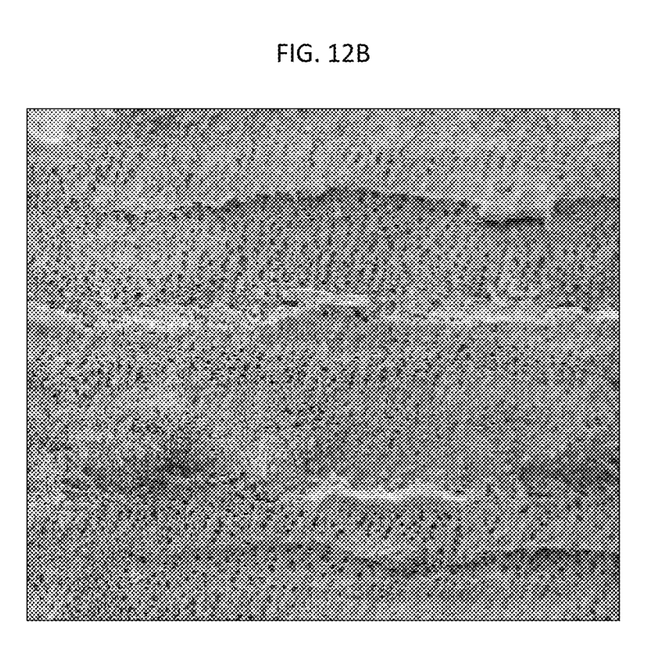

The 3D articles retained porosity as can be seen in a SEM cross-section view (FIG. 12A and FIG. 12B).

Example 2

A uniaxially expanded ePTFE tape was made by the process described in U.S. Pat. No. 3,953,566 to Gore. The porous tape was imbibed with a THV (a terpolymer of tetrafluoroethylene, hexafluoropropylene and vinylidene fluoride) that was dissolved in methyl ethyl ketone (MEK). The solution was applied via slot die coating process to the membrane. The tape was completely filled by the polymer, indicated by its clear look. The ePTFE-THV composite film had a thickness of 12 μm.

A 100 mm×100 mm aluminum platform (build plate) and two-sided adhesive tape (3M™ 950 described above) were provided. The two-sided pressure sensitive adhesive increases base layer adhesion but allowed for later removal of the PTFE layers.

The THV imbibed ePTFE membrane was applied on the pressure sensitive adhesive using a hand roller. The build plate was inserted in the edge of a laser cutter platform (TROTEC® Speedy discussed above).

Figure 13A:
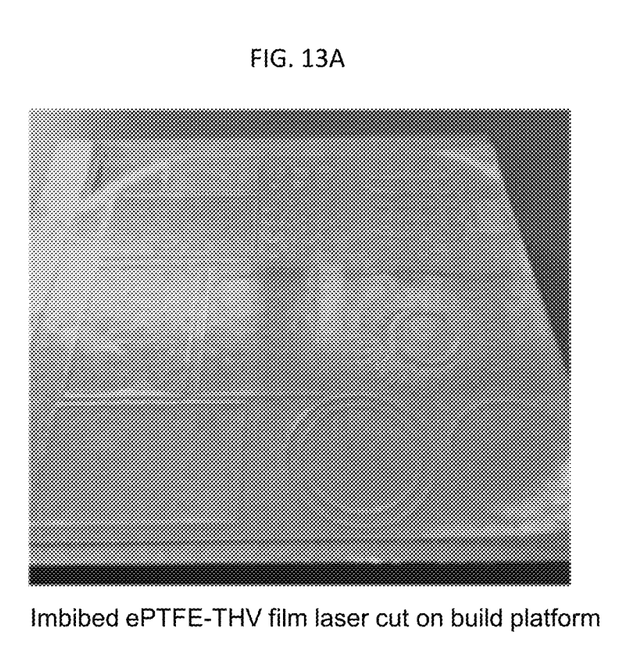
FIGS. 13A and 13B are images showing ePTFE imbibed with TVE (ePTFE-THV) and laser cut layers that may also be used in accordance with some embodiments.
Figure 13B:
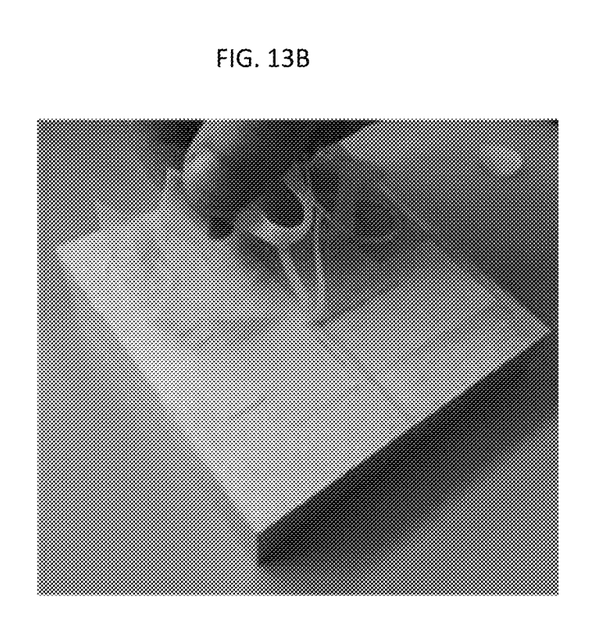

A two-dimensional pattern of one layer was created and transferred to the laser cutter software. Pre-trials were made in adjusting different settings of the laser cutter to be able to cut 1 layer of the ePTFE-THV film but not 2 layers (See, e.g., FIGS. 1 and 2). These settings where used for 20 layers. The laser was zeroed to the build plate. Re-zeroing the laser focus was redone for each ePTFE layer to assure that the laser was not out-of-focus. The first layer was then cut. FIGS. 13A and 13B are images showing ePTFE membranes imbibed with THV (ePTFE-THV) and laser cut layers.

Figure 5:
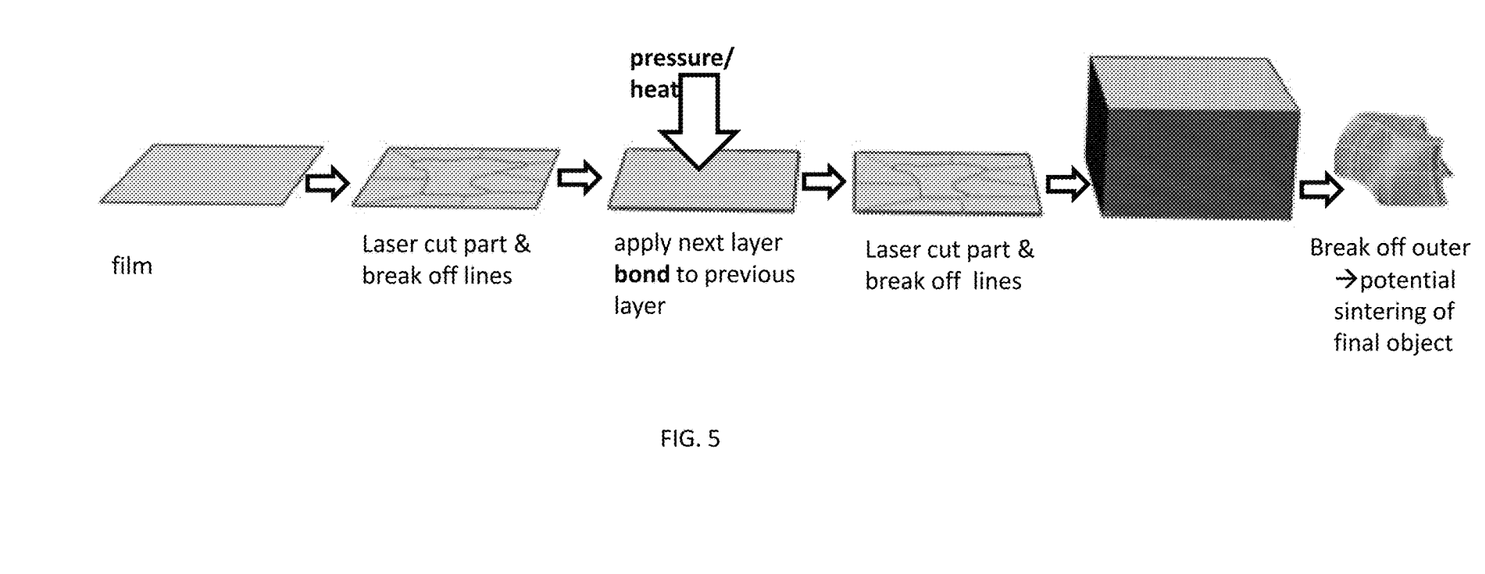
FIG. 5 shows an embodiment of a layer on manufacturing (LOM) process described herein in accordance with some embodiments.
Figure 6:
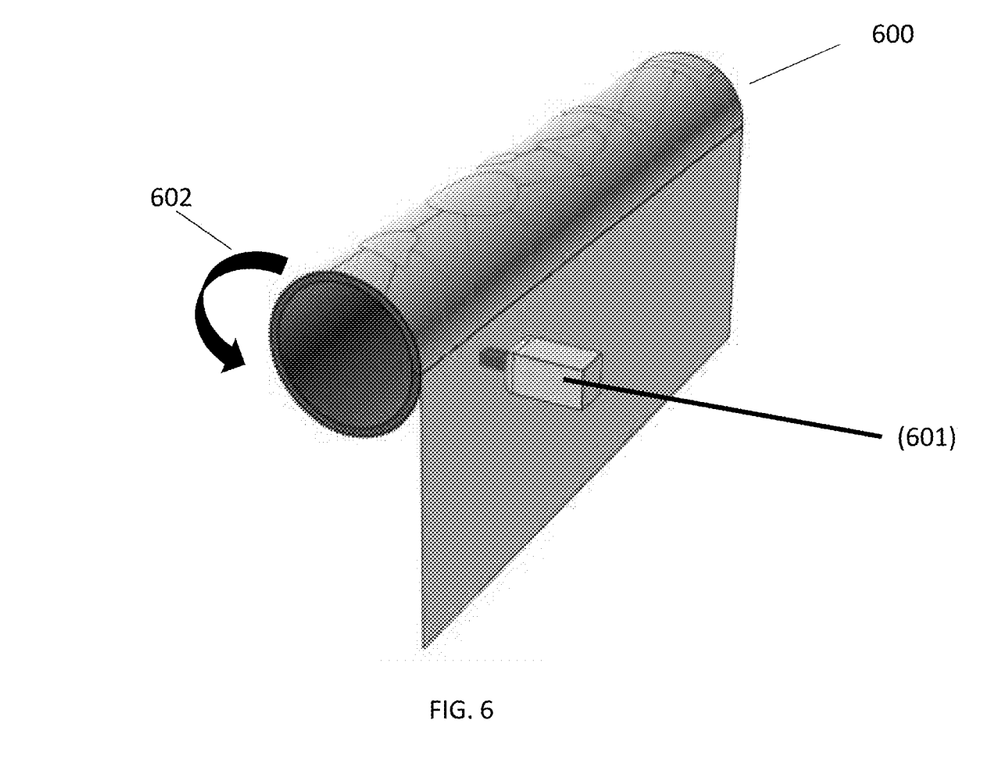
FIG. 6 shows a selective deposition lamination (SDL) having tubular orientation (600) for easier lamination and web handling of thin films in accordance with some embodiments.

A second layer of the ePTFE-THV film was then supplied and rolled onto the cut first layer at a 90° angle. The build plate with the two layers was removed from the laser cutter and inserted in a heat press (Sefa model MP 160). Heat press settings where 200° C., 5 bar, and 12 seconds. The process was repeated for an additional 20 layers. The parts were removed by cutting and breaking away the support structure (See FIG. 5). The parts did show an extraordinary balanced strength in all directions.

The invention of this disclosure has been described above both generically and with regard to specific embodiments. It will be apparent to those skilled in the art that various modifications and variations can be made in the embodiments without departing from the scope of the disclosure. Thus, it is intended that the embodiments cover the modifications and variations of this disclosure provided they come within the scope of the appended claims and their equivalents.

What is claimed is:

1. A process to form an integral three dimensional (3D) article from a plurality of expanded polytetrafluoroethylene (ePTFE) membranes consisting of:
   a. providing
      a base ePTFE membrane at least partially coated with an adhesive; and
      an additional ePTFE membrane at least partially coated with an adhesive;
   b. laser cutting the base ePTFE membrane into a desired pattern;
   c. bonding the additional ePTFE membrane to the laser cut base ePTFE membrane to form a multi-layered structure;
   d. laser cutting the bonded, additional ePTFE membrane in the multilayer structure into a desired pattern;
   e. bonding a further additional ePTFE membrane at least partially coated with an adhesive to the multilayered structure;
   f. laser cutting the further additional ePTFE membrane bonded to the multilayered structure;
   g. repeating steps (e), (f) or a combination of (e) and (f) until a desired 3D article is formed having a plurality of ePTFE membrane layers,
   wherein each ePTFE membrane layer has a porosity greater than 50%, and
   wherein the desired 3D article retained porosity in the process.

2. The process of claim 1, wherein bonding steps (c) and (e) comprise heating, pressing, or a combination thereof.

3. The process of claim 2, wherein the heating comprises a heat treatment of a sufficient time and temperature to melt or cure one or more of the adhesives.

4. The process of claim 1, wherein the base, additional, or further additional ePTFE membrane at least partially coated with adhesive is supplied as a continuous sheet.

5. The process of claim 1, comprising an initial step of forming a 3D pattern used to determine the desired pattern for each laser cut ePTFE membrane layer in the multilayered structure.

6. The process of claim 1, wherein the adhesive is the same between the ePTFE layers.

7. The process of claim 1, wherein is at least one of the plurality of ePTFE membrane layers is partially coated with adhesive and the adhesive is patterned to form hinges or micro-fluidic channels within the multilayered structure.

8. The process of claim 1, wherein the laser cutting of steps (b), (d), (f), and (g) use a laser beam focused to cut only one layer of ePTFE membrane per pass.

9. The process of claim 1, wherein the adhesive is different between the ePTFE layers.

10. The process of claim 1, wherein the 3D article is an implantable medical device.

11. The process of claim 1, wherein the 3D article is a biological fluid sampling device comprised of one or more micro-fluidic channels.

* * * * *